(12) United States Patent
Gurin

(10) Patent No.: US 12,321,871 B2
(45) Date of Patent: *Jun. 3, 2025

(54) CONTAMINANT INHIBITION PATHWAY CONTROL SYSTEM

(71) Applicant: Michael Gurin, Glenview, IL (US)

(72) Inventor: Michael Gurin, Glenview, IL (US)

(73) Assignee: Michael Gurin, Glenview, IL (US)

( * ) Notice: Subject to any disclaimer, the term of this patent is extended or adjusted under 35 U.S.C. 154(b) by 270 days.

This patent is subject to a terminal disclaimer.

(21) Appl. No.: 18/099,964

(22) Filed: Jan. 22, 2023

(65) Prior Publication Data

US 2023/0162070 A1    May 25, 2023

Related U.S. Application Data

(63) Continuation of application No. 16/368,172, filed on Mar. 28, 2019, now Pat. No. 11,574,222.

(60) Provisional application No. 62/648,951, filed on Mar. 28, 2018.

(51) Int. Cl.
| | |
|---|---|
| *H04L 9/06* | (2006.01) |
| *G06F 9/48* | (2006.01) |
| *G06N 7/00* | (2023.01) |
| *G06N 7/01* | (2023.01) |
| *H04L 9/08* | (2006.01) |
| *H04W 4/021* | (2018.01) |
| *H04L 9/00* | (2022.01) |

(52) U.S. Cl.
CPC ............. *G06N 7/01* (2023.01); *G06F 9/4881* (2013.01); *H04L 9/0643* (2013.01); *H04L 9/0872* (2013.01); *H04W 4/021* (2013.01); *A61L 2202/14* (2013.01); *H04L 9/50* (2022.05)

(58) Field of Classification Search
CPC ........ G06N 7/005; G06N 7/00; G06F 9/4881; G06F 9/48; H04L 9/0643; H04L 9/0872; H04L 2209/38; H04L 9/06; H04L 9/08; H04W 4/021; A61L 2202/14
See application file for complete search history.

(56) References Cited

U.S. PATENT DOCUMENTS

2019/0108060 A1*  4/2019  Outtagarts .......... G06F 9/45558
2020/0296093 A1*  9/2020  Hoyos .................. H04L 9/3247

* cited by examiner

*Primary Examiner* — Quazi Farooqui

(57) ABSTRACT

A system and method for contaminant control, often infection control, with multiple time and space domains that integrate active and passive infection control devices and processes that preferably feature infection control active additives with controllable dispassivation to limit post-consumption environmental impact. Additionally, the system executes the infection control devices and process transactions by controlling the dispatch of infection control tasks centered around a potential infection control incidence and/or cross-contamination locations from assets or personnel having probabilistic infection rates to increase compliance of infection control preventative measures.

20 Claims, 7 Drawing Sheets

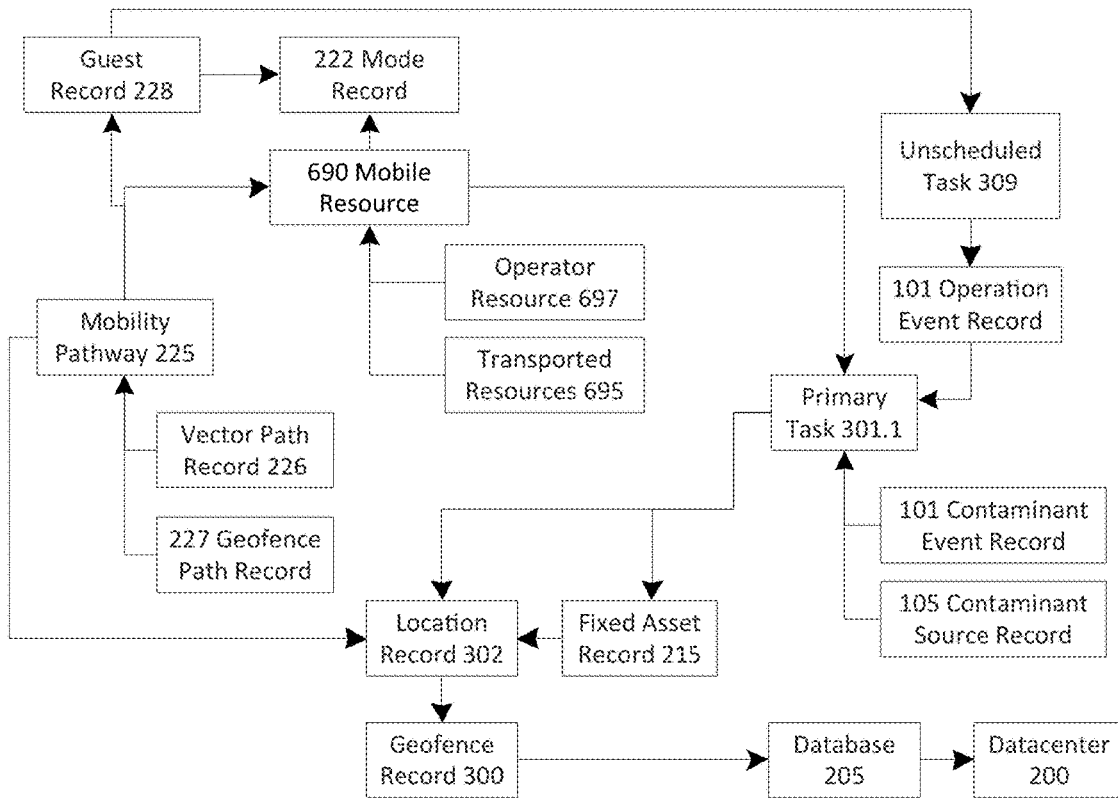

CONTAMINANT INHIBITION PATHWAY CONTROL SYSTEM

CROSS-REFERENCE TO RELATED APPLICATIONS

This application claims the benefit of provisional patent application No. 62/648,951 titled "Contaminant Inhibition Pathway Control System" filed on Mar. 28, 2018, and hereby incorporated by reference in its entirety. This application also claims the benefit of patent application Ser. No. 16/368,172 titled "Contaminant Inhibition Pathway Control System" filed on Mar. 28, 2019, and hereby incorporated by reference in its entirety.

This patent document contains material subject to copyright protection. The copyright owner, also the inventor, has no objection to the reproduction of this patent document or any related materials, as they appear in the foes of the Patent and Trademark Office of the United States or any other country, but otherwise reserves all rights whatsoever.

FIELD OF INVENTION

The present invention relates to a system comprised of multi-modal contamination prevention components ranging from "instant" disinfectant methods to long-term persistent contaminant inhibition methods integrated into a cohesive system to statistically reduce the transmission pathways of contamination. Contamination, whether it be viruses, microbes, toxins, or other harmful substances between recipients of such contaminants (whether it be animals, people, other healthful microbes, etc.) is a complex matter. The present methods of limiting the transference of contaminants between recipients is inadequate as one exemplary use case is the ever-increasing incidence of healthcare acquired infections "HAI".

BACKGROUND OF INVENTION

Prior art includes the deployment of disinfectant, otherwise known as "immediate" killing methods, or cleaning methods that remove contaminants at a specific time (hereinafter referred to at time zero, meaning immediately after the implementation of the disinfectant method. It is understood that immediate methods are hereinafter inclusive of decontamination cleaning and immediate disinfectant. It is further understood that the term immediate is collectively referred to measures that take place within approximately 7-10 minutes or less, but do not inherently have any persistent impact post the immediate (decontamination) method.

Other methods of include the deployment of persistent, otherwise known as long-acting killing methods, such that the specific time of impact is long-term (i.e., greater than 5 hours). The known in the art persistent methods however are relatively slow in action time, meaning the time required to prevent transference is greater than 2 hours and in most cases is approximately on the order of 24 hours. Such exemplary methods include the use of heavy metals such as silver, copper, zinc, etc. Hereinafter this category of methods is referred to as long-acting persistent methods.

A new in the art method is a fast-acting persistent killing method, such that specific time of impact is long-term (i.e., greater than 5 hours) yet the time required to significantly inhibit transference is less than 30 minutes and preferably less than 10 minutes and particularly preferred less than 5 minutes. Hereinafter this category of methods is referred to as fast-acting persistent methods.

The introduction in a wide range of deployments of autonomous or semi-autonomous mobile resources, such as delivery "on-ground" drones (e.g., shuttles moving product from point A to point B such as in a hospital) or cleaning "on-ground" drones (e.g., roaming vacuum cleaner or floor-washer equipment) enable the performance of tasks. This invention is accompanied by a further invention included in its entirety by reference in which the scheduling of primary tasks (e.g., logistics) with intermediate secondary tasks (cleaning) is enabling in a further reduction of contamination between contaminant pathways (i.e., cross-contamination incidence at a convergence point occurring at a convergence time in which a specific disease state is transmitted "known disease state", though the known disease state may not be actually known at the convergence time but rather in the future as a specific mobile resource becomes identified with said disease state). The system maintains for each disease state a range of parameters including methods of contamination, minimum incubation period, maximum dormancy period, and minimum decontamination time. The system also maintains specific information as it becomes available for each transmitter of a disease source "infection disease source", which can include personal and medical history data.

Prior art also includes the utilization of convergence or intersection points along a pathway in physical space yet doesn't integrate real-time incidence reporting or more importantly a fundamental recognition of decontamination methods to establish true cross-contamination convergence points (hereinafter referred to as "true-cross points". A true-cross point is a time and space domain having a cross-contamination probability greater than 0.1% (and preferably greater than 1%, particularly preferred being greater than 5%) in which recipients (meaning any object in which transference between a first contaminated object either suspected of or known to be a contaminated object to at least a first non-contaminated object or at least an object in which that object has a lower probability before the convergence within the true-cross point as compared to the relatively higher probability after the convergence within the true-cross point.

Prior art such as scheduling systems for task management also fail to fundamentally integrate resource optimization in which tasks are both location and time constrained. And certainly, fail to schedule mobile resources to dynamically minimize the probability of cross-contamination within true-cross points.

A need exists to maximize the effectiveness of a comprehensive system to actively and proactively manage contamination pathways in order to significantly reduce the transference of contaminants.

SUMMARY OF INVENTION

The present invention is a dynamic resource system "DRS" having active and passive decontamination methods in an integral and networked functionality amongst a fleet of mobile resources operational to perform both primary and secondary tasks. Such decontamination methods can be either stationary or mobile, with the latter being a mobile decontamination resource performing the decontamination method for a minimum amount of time being the decontamination task time. The decontamination task time is optionally a function of the speed of interaction between the cross-contamination source at the convergence point therefore having a direct relationship to the calculated cross-contamination probability.

A further object of the invention is to reduce the statistical probability of cross-contamination transference within true-cross points.

Another object of the invention is to utilize true-cross points to identify potentially exposed objects resulting from a known contamination incident.

Yet another object of the invention is to utilize a history of known contamination incidents to identify potential contamination hotspot (i.e., physical space domain or otherwise a known object within a known geofence) in which contamination is potentially transferred to objects passing within the contamination hotspot. When the disease state can be linked to the contamination hotspot it becomes identified as the disease state hotspot.

A further object of the invention is to reduce cross-contamination pathways by utilizing at least one immediate decontamination method with at least one fast-acting persistent decontamination method. Any of the decontamination methods can be active or passive, such that passive methods have an active agent (having recognized killing methods of pathogens including a categorization of effective pathogens). The preferred active agent thermally disassociates (i.e., heat to a critical decomposition temperature) to a material composition greater than 95% water and carbon dioxide, which is characteristic of organic materials. The particularly preferred active agent is void of nanoscale additives and metals, metal oxides, and metal salts for multiple reasons including the fouling of heat exchangers limiting energy recovery during thermal disassociation.

Another object of the invention is to select the most appropriate decontamination method such that active agent persistence time is greater than a regularly scheduled reapplication maintenance time interval and has a killing (or reproduction limiting) rate faster than the average time interval at the location of deployment.

Yet another object of the invention is to reduce cross-contamination pathways by utilizing at least one fast-acting persistent decontamination method having a fast-acting decontamination reduction time between 10 seconds and 10 minutes with at least one fast-acting persistent decontamination method having a fast-acting decontamination reduction time between 5 minutes and 1 hour such that the combination of the two decontamination methods achieves a statistical cross-contamination reduction of at least 10%, preferably at least 25%, and particularly preferred at least 50% lower than either of the methods alone.

Another object of the invention is to utilize at least one continuity pathway for a mobile resource such that the at least one continuity pathway is a time and space domain pathway of air, water, food, task operational equipment, non-food consumables (e.g., pharmaceuticals, nutraceuticals, nutrients, etc.) or personnel.

Yet another object of the invention is to utilize true-cross points for at least two continuity pathways to identify potential sources of contamination in which a known contamination incidence occurred.

Another object of the invention is to monitor the time interval, whether it be minimum, maximum, or mean or average, of contact at a potential contamination hotspot such that the system deploys a fast-acting persistent decontamination component with a decontamination reduction time faster by at least 1 second than the time interval threshold target. The time interval threshold target is preferably at least one second less than the minimum time interval of contact, though often practically the time interval threshold target is at least one second less than the average time interval between contacts.

Yet another object of the invention is to provide an active indicator to advise a potential recipient of a contaminant an insufficient decontamination time subsequent to then recent contact at a potential contamination hotspot and the minimum time required to reduce contamination potential by at least 50% of preventative decontamination methods implemented at the potential contamination hotspot.

Another object of the invention is to provide an active scheduler of a mobile resource having an active method to decontaminate a potential contamination hotspot as a secondary task when the mobile resource has the opportunity to pass within the potential contamination hotspot when an insufficient decontamination time subsequent to then recent contact at a potential contamination hotspot and the minimum time required to reduce contamination potential by at least 50% of preventative decontamination methods implemented at the potential contamination hotspot has taken place.

Yet another object of the invention is to have a mobile resource configured with at least one fast-acting persistent decontamination method having a fast-acting decontamination reduction time less than the time it takes for the mobile resource to travel from a first exposure point to a potential contamination incident and a second exposure to a potential recipient of the contaminant from the first exposure point. It is a further object of the invention that the system dynamically alters the fast-acting decontamination reduction time as a function of varying operating conditions at the potential contamination hotspot.

Another object of the invention is to have a mobile resource configured with a dynamically variable operating active decontamination method, such as an ion generator, such that the active decontamination method operates in a first mode having a relatively concentrated impact on a potential contamination hotspot (by at least 10%, preferably at least 50%, and particularly preferred at least 80%) as compared to a second mode in which the decontamination is non-concentrated and provides general air decontamination or surfaces in which the mobile resource passes by. The preferred decontamination method is virtually an entirely solid-state device such that a MEMS device enables switching between the first and second modes, and that the solid-state device provides ion generated wind, as known in the art, is substantially void of ozone (i.e. less than 1 ppm and preferable less than 10 ppb) so as to provide general air quality improvements as a secondary task when not passing a specific potential contamination hotspot. A prioritization of secondary tasks is performed such that the secondary task is a decontamination method on a potential contamination hotspot in accordance to hotspots that have either the highest probability of cross-contamination or the highest cost risk associated with a known (though could be probable) contaminant at the specific hotspot.

It is another object of the invention to manage the aggregate collection of individual decontamination methods such that the decontamination method impact on disposal methods is minimized. One such embodiment is an antimicrobial active in which the disposal of the decontamination method (or object in which the decontamination method is placed on) is important is the potentially adverse impact on waste-water treatment systems. Known in the art waste-water treatment systems rely on microbial action to properly return waste-water to a reusable state, therefore any residual antimicrobial effect from the decontamination method has the potential to adversely impact waste-water treatment systems (or even garbage dumps). It is therefore an object of the invention to utilize antimicrobial methods such that the time of decontamination impact approximately expires prior to the disposal interaction (or is at least minimized). The selection of an antimicrobial method such that a relatively short exposure to temperature conditions greater than 200 Celsius decomposes the antimicrobial active to gases comprised solely of carbon monoxide, carbon dioxide, or water. It is understood that residual nitrogen containing substances or gases would have minimal impact on any disposal measures. This is contrary to the class of antimicrobials containing heavy metals (e.g., copper, zinc, silver, etc.) in which thermal decomposition produces residual salts that have an adverse impact on downstream equipment (e.g., heat exchangers, incinerators, etc.). It is preferred that the decomposition of the antimicrobial takes place at a temperature less than 600 Celsius (and preferably less than 350 Celsius). Another embodiment of the invention is the use of additional antimicrobial decomposition methods at lower temperatures such as known in the art supercritical water oxidation, ozone treatment, or ultraviolet light all having in common the goal of decomposition being the avoidance (i.e., void of) metals or metal salts and the desire of decomposition byproducts being virtually entirely gases (e.g., $CO_2$, CO, or $H_2O$).

It is yet a further object of the invention to minimize the system aggregate potential for cross-contamination while concurrently minimizing the downstream impact of decontamination methods (i.e., antimicrobial) post-usage of the decontamination method within the primary ecosystem (e.g., hospital, food processing plant, patient care, etc.). The preferred means is to utilize an antimicrobial system such that the antimicrobial system is comprised of an otherwise unstable active (e.g., essential oils, lignin oils, botanicals, etc.) such that a controlled release of the unstable active reduces by at least 20% the potential for the unstable active to adversely impact post-useful life of the object in which the antimicrobial has been embedded. A particularly preferred composition is such that the unstable active has a triggered release point, such that the essential oil is no longer captive within a stabilizing matrix and therefore evaporates away. Such a triggered release point can be a biodegradable binding matrix, a temperature triggered decomposition first of the binding matrix, or a water-soluble binding matrix such that a water activity level is sufficient to ensure water migration and therefore release of the unstable active.

It is an object of the invention to dynamically configure substrates within a controlled ecosystem (e.g., hospital, etc.) with specific decontamination methods to optimize a statistical reduction of contamination potential balanced by the post-use life impact of the decontamination methods and their associated costs within the controlled ecosystem. It is yet another object of the invention such that controlled ecosystem maintains, regulates and controls pre-use conditions (e.g., temperature and relative humidity), time of use conditions (e.g., monitoring length of use time and temperature and relative humidity conditions, as well as any use-specific conditions such as medical condition of patient), subsequent post-use conditions, scheduled post-use treatment including time duration and temperature processing conditions prior to known disposal (or otherwise known as final disposition) external of controlled ecosystem.

A further object of the invention is to dynamically configure and route mobile resources such that successful completion of primary tasks are realized while scheduling intermediate secondary tasks to optimize a statistical reduction of contamination potential balanced by incrementally higher travel times and costs associated with incrementally higher travel distances by the mobile resources.

All of the aforementioned features of the invention fundamentally recognize the integration of cross-contamination pathways in the time and space domain with dynamically configurable decontamination methods being an important system to substantially reduce the cost and damage associated with contamination incidences, particularly as further implemented using multi-modal mobile resources within the ecosystem being controlled by the control and management contamination impact system.

BRIEF DESCRIPTION OF DRAWINGS

FIG. 5 is a data structure for the mobile resource.

FIG. 6 is a data structure for the mobile resource use case of decontamination transporter.

DEFINITIONS

Figure 1:
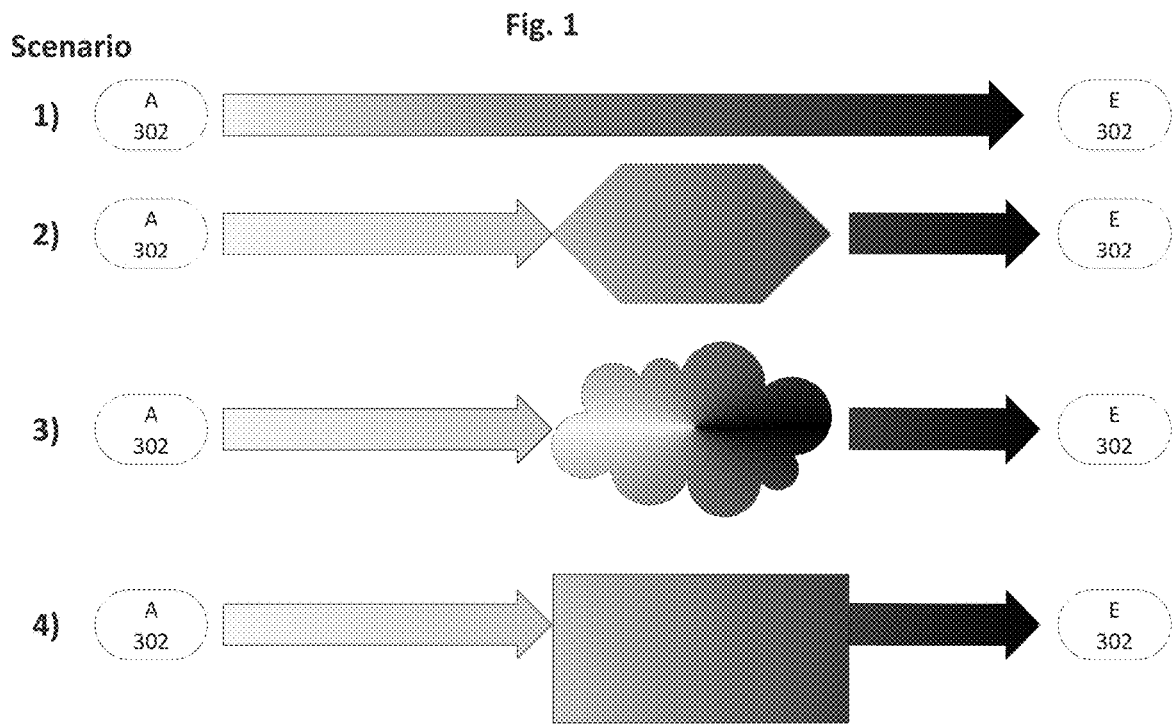
FIG. 1 is a top view illustration, having multiple scenarios, of vectors with probability gradients.

The term "mode" is a characterization of a mobile resource into segmented context by at least two locations, one of the current location and the other of a dynamically altering location as a function of time, co-located mobile resources, or adjoining geofences. The preferred embodiment determines mode through the utilization of at least three locations comprised of current location, past location(s), future location(s) centered around a specific user. The particular preferred embodiment determines mode by at least three locations for multiple interacting users.

DETAILED DESCRIPTION OF INVENTION

Here, as well as elsewhere in the specification and claims, individual numerical values and/or individual range limits can be combined to form non-disclosed ranges.

Exemplary embodiments of the present invention are provided, which reference the contained figures. Such embodiments are merely exemplary in nature. Regarding the figures, like reference numerals refer to like parts.

The invention significantly reduces the incidence and contamination of contagious disease states across the combination of multiple time and space domains.

Pathways of Cross-Contamination

The location(s) of potential true-cross points is vital to determining the cause and effect of a cross-contamination incident. The determination of location, as established by concurrently filed patent on location determination is noted below for reference.

In addition, the establishment of pathways is important in contamination determination notably as specific pathways have specific disease states in which transference of contaminants can take place. For example, E. coli is a disease state largely associated with contaminated food. The incidence of Legionnaires is associated with contaminated water.

The system features multiple pathways, each pathway having a probability function for each disease state of importance within the overall ecosystem. The pathways include individual pathways that are preferably represented by a vector having both a time and space domain, which is further represented by a probability mapping to fill in location gaps understanding that the most important location mapping being for potential contamination hotspots. The preferred embodiment of the system has pathways, such as in a hospital, for each employee, each patient, each piece of equipment notably mobile resources, and for each delivered utility such as air (purified and conditioned air from an HVAC system), water, food, pharmaceuticals/nutraceuticals, etc. Each pathway is further comprised of potential contamination hotspots, with hotspots ranging from common area items (e.g., elevator buttons, door handles, etc.) to patient room items (e.g., bed trays, bed rails, patient monitoring and/or dispensing equipment). Mobile resources include shuttles for the delivery of food, movement of patient biological samples (e.g., blood, urine, etc.), delivery of pharmaceuticals from the pharmacy, patient wheelchairs or pre-surgical or diagnostic testing gurneys, cleaning devices such as floor cleaning, vacuum cleaners, wall cleaners or even roaming decontamination equipment whether dedicated mobile resources or multi-functional mobile resources such that a cleaning piece of equipment has onboard means to further decontaminate hotspots (i.e., an ion generator focused onto a hotspot as the mobile resource moves between a departure point and an arrival point to perform a specific primary or secondary task).

As noted earlier, a critical feature of the system is to determine the location of a mobile resource accurately, at least relative to a location in which a task must be performed. An even more critical feature of the system is to determine converging intersection points on a time and space domain (i.e., overlapping vectors predominantly matter when they occur in approximately the same time). It is an object of the system to represent location, as represented by a vector when it is precisely and accurately known in a gradient (preferably a color, or as known in the art any numerical representation of a color or pattern that varies as a function of time (such that like colors represent like time) and from the start of the vector to the end of the vector based on time. When location is not precisely known, it is represented by a geofence. The geofence is optimally represented by a varying probability gradient, in which the probability gradient provides a relatively higher projection of actual location likelihood. The probability gradient is established by the combination of historic records establishing a pattern of travel times between known precise locations (e.g., points in which known tasks are performed at known locations, or GPS determined locations in which it is known that location error is less than a specific error threshold limit in percentage or absolute length) such that future times in which travel between the same known locations enables an increased accuracy of precise locations in between those same known locations (that otherwise have location errors that are beyond the specific error threshold limit. The location vector has an integral color (or pattern) that varies along the time domain, such that the key differentiation is a visually recognizable similarity function (i.e., the human eye or graphical processing unit recognizes the color or pattern at a point of convergence as being approximately identical, at least within a similarity threshold limit). When the location has a degree of uncertainty the location vector is represented by a geofence vector having an integral color (or pattern) along with an optional probability profile (or a probability map of individual locations based on known prior high-certainty locations, or additionally in combination with future known (or anticipated) high-certainty location(s) when looking forward in time). This feature of the invention also enables superior accuracy of retroactive location gap filling.

The system aggregates as many as possible historic records for each recognized contamination point. The aggregated historic records are utilized to calculate the time interval between sequential and subsequent contamination points at the contamination time. The particularly preferred system continuously monitors and assigns (re-assigns) infection control methods as specific determined from a range of decontamination methods including persistent infection control device or process or material composition having an active agent, fast-acting infection control device or process to reduce an incidence or contamination of infection rate by at least 5% greater than the maximum of an individual decontamination method or even the dispatching of an immediate disinfection method (e.g., UV or chemical disinfection or ion generator or ozone, etc.) with a minimal goal of reducing the probability of cross-contamination by at least 50% for each contamination point based on the statistical median calculated time interval at the respective contamination point. The particularly preferred goal is reducing probability of cross-contamination by at least 80%, or specifically preferred goal by at least 90%.

Known locations are established by multiple means including the performance of a task through a device having a known location in which the device communicates via wired (e.g., Ethernet) or wireless (e.g., low-energy Bluetooth, NFC) such that the highest accuracy of location is established by either the fixed location Ethernet or the wireless method with the lowest range.

It is a feature and an object of the invention to fill in the gaps of location knowledge, whether the prior knowledge of a precise location is not known at all or the location is represented in the past by a geofence (preferably with a probability gradient), such that the gap(s) is replaced by a precise vector (or simply a geofence having a more precise probability gradient). One instance in which precise location knowledge is desired, even though the mobile resource is no longer at that location, is in establishing likelihood of cross contamination retroactively after an infection has been obtained, transaction fraud prior to the shipment of an ecommerce order, and projections of future location when resources travel relatively repetitive routes (such as employees within a hospital). It is a feature and an object of the invention to maintain historic location data as obtained in real-time for each location (preferably on a continuous vector mapping) with a set of non-real-time adjusted location data such that the combination of the real-time location and the non-real-time location adjustment provides a more precise predicted real-time location. It is understood that the non-real-time location adjustment is a function of at least one of the precise location or the real-time location point. The non-real-time location adjustment is preferably also a function of the actual mobile resource and optionally also as a function of time. The particularly preferred non-real-time location adjustment is further as a function of a known presence of an at least a second mobile resource object or an at least first inanimate object (which can have more than one position e.g., door that is open or closed) that in fact impacts the location precision when the first mobile resource is in proximity with the at least a second mobile resource. Retroactive improvements of location data occur by analytical inclusion of subsequent data records through knowledge of then future performance of primary tasks or secondary tasks at known locations. More specifically, there are gaps of precise (or even general) location knowledge that occur (most notably from loss of location-determination signals e.g., global positioning systems "GPS" whether the GPS is an indoor or outdoor GPS or simply uses wireless triangulation as known in the art) such that during the occurrence of a particular task (or event, such as opening a door as the mobile resource moves between locations) the precise location is not yet known. Yet, when the mobile resource performs a task or event at a both known time and known location (or within a known geofence) this action establishes a probability profile for past tasks or events (in other words, if a task took place on the $2^{nd}$ floor of a hospital at 11:00.00 AM there is a very low probability that the same mobile resource would be on a floor above or below the $2^{nd}$ floor at 10:59.50, especially if the location is not near an elevator or staircase, or if it is known with certainty that no mobile resource was located in an elevator or staircase in between those times). The inventive system uses both known occurrences of an at least one second task in terms of precise time and location, and/or known absences of tasks in terms of precise time and location, or combinations thereof to establish a location probability for a first task in terms of precise time and location that is a function of precise time and location for the at least one second task, and/or for the known absence of tasks within a precise location (or geofence) within a known time range.

It is another object of the invention to create a comprehensive record of location as a function of time for each mobile resource, recognizing that a mobile resource can be a person guided device, a semi-autonomous or autonomous guided device, or even a person qualified to execute primary and/or secondary tasks such that the person is mobile and the device that the person uses has no independent means of movement. When location data is for a specific person the maintenance of personal privacy is essential. Yet, serving the specific person (i.e., operator) with superior precision requires extraction of location knowledge. It is an object of the invention to segment the access to personal location data notably by leveraging a distributed database (with multiple encryption keys, preferably with access control by a function of both a mode and a geofence) also referred to as a distributed ledger such that the distribution of location data is by at least one of a) mode, b) geofence, or specific data server representing location data by a combination of mode and geofence. It is recognized that specific geofences maintain data that is not only proprietary to the individual person but also business or contextually sensitive to the host business/purpose of that specific geofence. One exemplary host business is a hospital (or medical campus) in which strict privacy laws provide guidance and control of access to sensitive location data linked to a specific individual person. Yet, it is an object of this invention to repackage this highly sensitive comprehensive location into reduced sensitivity packets. The distributed ledger of location data is segmented by mode (e.g., exercise, home, work, medical, personal, etc.) even within a private geofence. Specifically, the distributed ledger database preferably utilizes rules-based logic and mode functions to create location offsets in which the offset is a function of time, mode, and/or rules-based logic or combinations thereof. The purpose of a location offset is to ensure that the absolute location can't be accessed, yet relative location data can be accessed. One exemplary incidence in which relative location information is desired but absolute location information needs to remain private is an exercise application such that the exercise application desires to calculate or track data including number of steps, calories burned, velocity and/or acceleration rates etc. yet the actual instance that the absolute location is within a hospital or an armed forces forward operating base must remain secret. In the context of a hospital environment a staff member such as a physical therapist is authorized to track physical activity but should not have knowledge of specific activities such as bathroom activity, medical testing procedures, etc. In other words, access to specific location information is a function of at least mobile resources (i.e., the mobile resource requesting information and the mobile resource owning the information). Location offsets are preferably encrypted utilizing a non-linear or linear function that can be further switched between varying non-linear or linear functions in accordance to further rules-based logic as a function of time. Personal location data is segmented into access type between public and private. Private data is provided within the guidelines of secure access in packets that include at least: a) summary of mode data, b) redacted data of specific modes such as healthcare specific modes, c) segmentation data by mode outside of healthcare specific modes, and d) data containing offsets.

The system incorporates a process to utilize the individual collection of pathways as represented by vectors having location/space and time domains. An important feature is such that every potential contamination hotspot, also just referred to as "hotspot", has detailed database of mobile resources that pass through the hotspot whether the hotspot represented by a specific tightly referenced location point or a geofence such that at a minimum the mobile resource entry and departure time is provided for each hotspot. In the event of a contamination incidence event, the time and location of such incidence event is utilized to determine potential contamination hotspots with their respective probability mappings for each disease state taking into account all of the converging pathways and their respective hotspots. The system monitors, tracks, calculates, and dispenses a probability report for each linked potential hotspot to the initiating contamination incidence event. The system then subsequently dynamically configures at least one method to reduce contamination potential with the specific goal of reducing the statistical probability of a incidence event recurrence (whether it be for a same disease state, such as a microbial cluster in a surgery sink, or a different disease state, such as a human resource failing to practice consistent or thorough hand-hygiene practices).

It is another feature of the system such that a frequency interval for an immediate decontamination method is increased at hotspots having a relatively higher contamination incidence events. Another feature of the system is dynamically altering an embedded decontamination method at the hotspot such that the time to decontamination probability reduction is decreased so as to accelerate decontamination process by accelerating the release of an otherwise unstable decontamination active so as to reduce the probability of transference.

Variable Decontamination Rate

A fundamental feature of the system is the dynamic configuration of the decontamination method, notably the rate in which at least an approximate 10% statistical reduction of cross-contamination is achieved (though preferably at least 25%, particularly preferred at least 50%, and specifically preferred great than an 80% statistical reduction in contaminant transference. All things equal the faster the decontamination rate the less long-term persistence time; thus, the decontamination rate is a balancing act between the requirement to replace the decontamination method (i.e., replace surface coating having active antimicrobial or "refresh" through reinfusion of otherwise unstable decontamination active into the coating) or implement a secondary task (e.g., immediate decontamination method such as ion generation, UV exposure, or application of disinfectant) so as to "reset" the hotspot to a clean state.

Lifecycle Impact

Virtually all decontamination methods have the potential to have an adverse impact on post-use downstream processes whether the adverse impact limits effectiveness of processes such as waste-water treatment, garbage disposal, or thermal heat recovery from thermal incinerators due to salt corrosion or scale formation. A significant feature of the system is the dynamic configuration of decontaminant methods such that post-use can be virtually eliminated through a thermal decomposition process converting the decontaminant method (i.e., antimicrobial notably an otherwise unstable active) into non-harmful gases (e.g., carbon dioxide, water/steam, carbon monoxide, and potentially with nitrogen gas).

The inventive system utilizes an HAI detection module to initiate the step of converging on a common convergence point in the time and space domain for determining a source of the HAI; utilize the history events of assets, employees, etc. to create a probabilistic assessment of the source, and to create and generate the dispatching of persistent, non-persistent, and fast-acting antimicrobial tasks; changing the time interval of non-persistent and fast-acting antimicrobial tasks proactively and monitoring the future incidence of HAI at the same source.

The inventive system utilizes a location-based system that monitors disinfectant processes, such as and including hand-washing or the otherwise application of fast-active disinfectant processes to establish a probability of disinfectant effectiveness for that respective individual disinfectant process for the respective HAI source and/or contamination asset. The probability of disinfectant effectiveness is normalized to a statistical representation of the respective HAI source for the full set of contamination assets (e.g., employees, carts across pathways), as well as variations for the respective contamination asset normalized to the range of HAI potential sources of the same category as a function of type of HAI potential source (e.g., hand-washing, application of fast-acting disinfectant process, application of persistent antimicrobial process, application of non-persistent antimicrobial process). Deficiencies (i.e., non-compliant tasks) at the HAI potential source and contamination asset leads to the dispatch of supplemental persistent, fast-acting, or non-persistent antimicrobial processes to offset the deficiency. Furthermore, the system modifies the contamination asset disinfectant effectiveness rating so that future probabilistic tasks are directly impacted on HAI potential sources as a function of the contamination asset and further as a function of time in combination with the specific space domain of the HAI potential source.

Yet another aspect of the HAI potential source is the time duration between a first and then a second contamination asset interaction at a respective HAI. The inventive system dispatches fast-acting or disinfectant application assets to apply antimicrobial measures to the HAI potential source asset, notably the application is deployed to assets ranging from personnel that already have a reservation that includes the movement from a first location to a second location in which the routing includes or can include an intermediate and temporary stop between the departure time from the first location and the arrival time at the second location. Exemplary assets include autonomous or semi-autonomous assets that are configured with at least one method of executing the disinfectant application measure. Another exemplary asset includes a person (e.g., notably an employee, or an integral measure on the HAI potential source asset) in which the system schedules a reservation to perform the disinfectant application measure. Yet another aspect of the system is the coordination of the disinfectant application measure, particularly a measure that is integral to an HAI potential source such that the system dispatches a reservation to switch between a short-range and a long-range disinfectant application measure. An exemplary of this short-range and long-range disinfectant application measure is a corona discharge device that has at least a two-position discharge range in which one of the at least two positions are at least 10% and preferably at least 50%, and particularly at least 90% of the smaller inhibition zone than the otherwise long-range disinfectant measure relative to the short-range disinfectant measure (e.g., an integral corona discharge device that in the short-range mode discharges ions onto a door handle, and that the long-range mode discharges ions broadly into the door passage area in which the door for the respective door handle swings open and close). There are multiple methods of varying the inhibition zone, including by limiting the discharge current further enabled by using wires having a small radius that has the further advantage of significantly reduced ozone production. The further combination of corona discharge to create ion wind, has parameters as known in the art, to vary ion discharge range so as to switch between modes in which the short-range (e.g., door knob) is subject to a fast-acting disinfection (such that disinfection occurs between subsequent and sequential touching instances), and a mode for broader disinfection in which the ions acting on the short-range (e.g., door knob) are minimized. It is a goal of the invention to switch between modes in which ions extend beyond the short-range by varying active electrode zone, discharge current, charge of the short-range smaller inhibition zone, ion wind emitting speed, and active electrode zone voltage while optionally also varying charge of the long-range larger inhibition zone.

Microbes have a negative surface charge and thus ions having positive charge are both attracted to their surface disturbing their electric balance therefore disrupting their electron transfer.

It is understood that references to Hospital Acquired Infections "HAI" are predominantly referenced in this invention, however the invention addresses all nosocomial infections, which are defined using the broader definition of an infection that is contracted because of an infection or toxin that exists in a certain location (also including day care, public spaces such as airports, trains, etc.) or transferred between and amongst people directly, or via dispersion or surface interaction. As a further point of reference, people now use nosocomial infections interchangeably with the terms health-care associated infections (HAIs) and hospital-acquired infections.

Combination of omniphobic low-adhesion smooth surface coating, ion wind generator having low ozone production, and corona discharge. The utilization of a smooth surface coating having low adhesion.

{optional} The coating further comprised of a persistence antimicrobial active. The coating having a static decay time of faster than 15 seconds at a relative humidity greater than 30% {preferably a static decay time of faster than 1 second, and particularly preferred of faster than 0.2 seconds} to reduce the attraction of microbes to the active surface. One exemplary material is Teslin as manufactured by PPG. This is a particularly important feature as people interact with the substrate and would otherwise experience static shock (an electrostatic discharge that rapidly achieves charge neutralization).

Solution is comprised of a substrate having a first portion and second portion of the substrate, with or without coating, having a static decay time faster than 15 seconds (preferably faster than 1 second, particularly preferred to faster than 0.2 seconds); an ion wind generator whereas the ion wind generator is configured in a mode to "vacuum" particulate away from the first portion of the substrate and a concurrent positive charge ions are generated to deactivate any of an at least one of virus or bacteria on the first portion or second portion of the substrate.

Further comprised of a wind channel whereas the wind channel directs the ions from the first portion to the second portion of the substrate.

Further comprised of a means to rotate or move the substrate such that the position of the first portion of the substrate is exchanged with the second portion of the substrate.

Further comprised of a filter downstream of the first portion of the substrate and downstream of the ion wind generator, and upstream of the second portion of the substrate. The preferred filter is also comprised of a substrate having a static decay time faster than 15 seconds. The particularly preferred filter has a coating to reduce adhesion of dust, viral, and/or bacterial contaminants. The specifically preferred filter has a homogenous porosity of less than 300 nanometers (yet preferred less than 100 nm, or less than 60 nm) in which the filter and its porosity is homogenous through a single layer.

Turning to FIG. 1, FIG. 1 depicts four scenarios of a vector starting at first location A302 to an ending location E302. Each vector can range from Scenario 1 that depicts an instance where the precise location is known from start to finish, Scenario 2 that depicts a region in which precise location is not known (such that the probability varies from an intermediary location in which two precise tasks occur at a precise location and precise time but in between those two tasks precise location becomes unknown and the time in between each task establishes a relatively linear probability gradient, Scenario 3 is similar to Scenario 2 except that probability gradient is not linear (such as where a wireless signal has more variation such as created by interference of doors, walls, etc.), and Scenario 4 in which no known information is available between the two precise tasks and therefore the probability gradient is large and relatively non-deterministic in between the two precise tasks.

Figure 2:
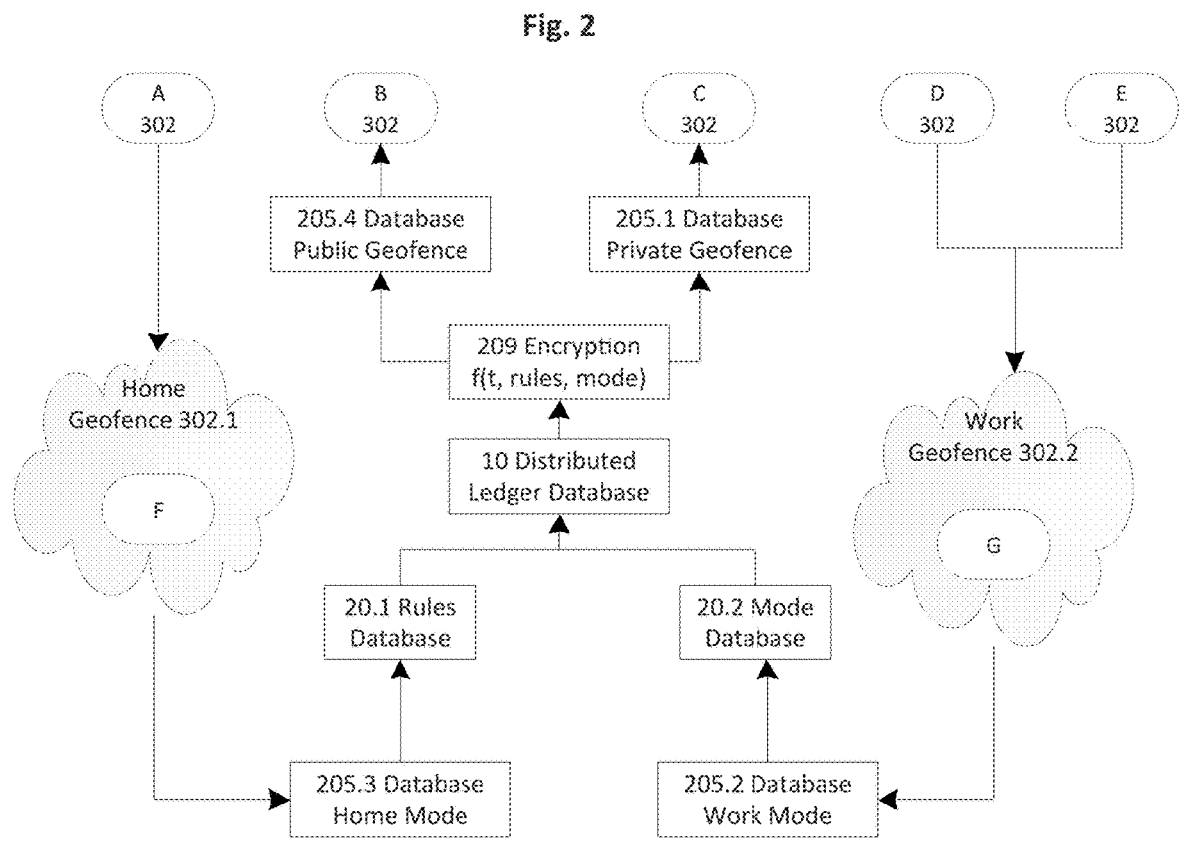
FIG. 2 is a data structure illustration for locations relative to geofence positions.

Turning to FIG. 2, FIG. 2 depicts the data structure for both contextual relevance as well as privacy constraints. Each location A302, B302, C302, D302, and E302 has a record with a parent-child relationship to at least one geofence. It is understood, though not depicted, that any location can have multiple parent-child relationships to multiple geofences with further record connectivity to Public Geofence Database 205.4 (as connected to location B302 which enables less severe access control relative to the Private Geofence Database 205.1 as connected to location C302). The utilization of a Home Geofence 302.1 (as connected with location A302) establishes a fundamental set of privacy rules in accordance to the Rules Database 20 in addition to the Home Geofence 302.1 also having a parent-child relationship to establish the geofence as within an at least one Home Mode with the Home Mode Database 205.3. Home Mode is particularly important in terms of privacy and therefore it is understood that specific Encryption function 209, which is a function of time, rules and mode, is used to severely limit access of such data within a Distributed Ledger Database 10. The Mode Database 20.2, another database similar to the Rules Database 20.1, maintains records of geofences in which relevant modes are possible and respectively relevant rules are possible. Information gathered within a home has particular relevance amongst a family (largely without restrictions) but also provides important marketing consumption info as one exemplary with another exemplary being cleaning or cross-contamination requirements). The performance of cleaning or decontamination tasks in between logistics transport from a first location to a second location within a home. A Work Geofence 302.2 (as connected to locations D302 and E302) also has specific meaning therefore requiring differentiation from other geofence categorizations.

Figure 3:
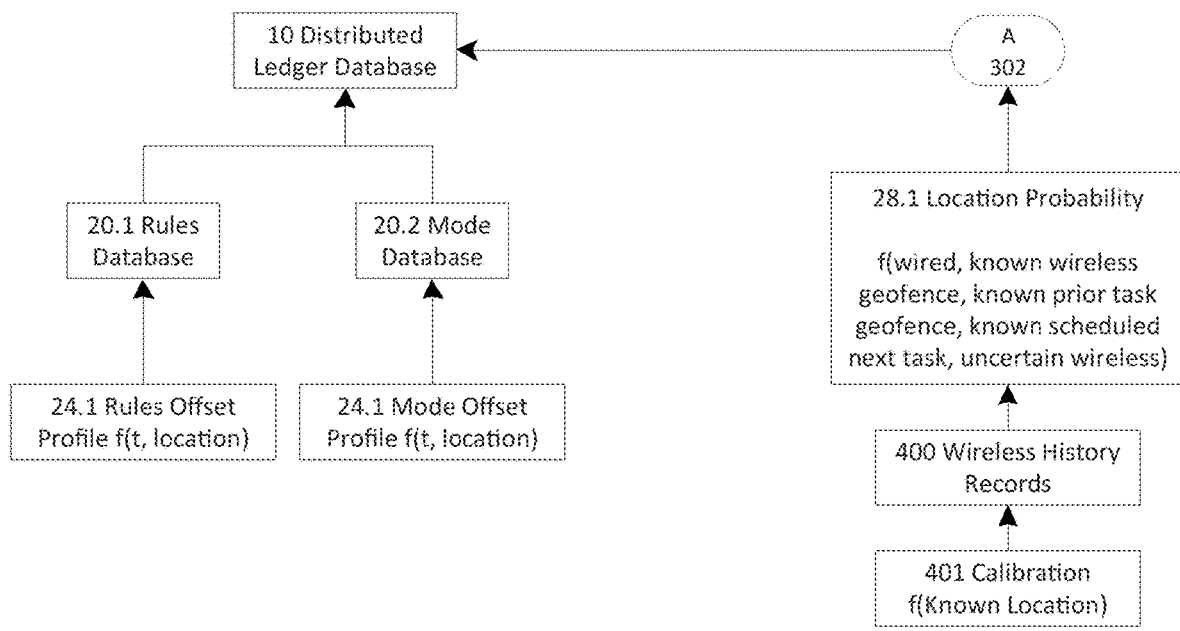
FIG. 3 is a data structure illustration for location specific records using mode as encryption key within a distributed ledger database.

Turning to FIG. 3, FIG. 3 depicts the data structure, in this instance for a mobile resource at location A302, such that the location determination is first improved by at least 5% accuracy through calibration function 401 as a function of at least one known location (i.e., having precise location e.g., accuracy of less than 0.5 meter or preferably less than 0.25 meter or particularly preferred less than 2 cm accuracy) and/or through wireless history records 400 in proximity relevant to this same location A302 (e.g., repetitive movement through a geofence in close proximity to this same location A302 yields wireless history records such as triangulation via known wireless communication methods including WiFi or Bluetooth as known in the art) establish a location probability 28.1 that is a function of wired locations in which tasks occur at a known time, known wireless geofence in which mobile resource wireless signal strength is known to be within said wireless geofence creating a subset geofence in which location A302 must be within, known prior task geofence having an associated known time yielding a calibration point for future use of wireless history records 400, known scheduled next task that provides an increased probability of movement towards the location in which that known scheduled next task must occur (i.e., if the mobile resource is on a $2^{nd}$ floor and the known scheduled next task is also on the $2^{nd}$ floor then movement from the known prior task geofence to the known scheduled next task has a very high probability of also being on the $2^{nd}$ floor and further in between the known locations of the known prior task geofence and the subsequent known scheduled next task), and an uncertain wireless (i.e., such as a repetitive placement of GPS on a different floor, such that the occurrence of the known scheduled next task 'geofence' actual time in combination with the occurrence of the known prior task geofence enables future (as well as retroactive) calibration of location vector despite the otherwise significant error in location. Once the more precise location is determined (whether for future or retroactively) a more precise location vector is created. The knowledge of precise location and location vector, particularly as a function of time, is extremely valuable for establishing intimate and highly personal (when the mobile resource is physically connected to a human) information and thus highly susceptible to privacy intrusions. Therefore, placement of precise location and location vectors requires both methods to enable authorized access to this information yet contextually segmented so as to ensure only proper authorized access to this information even though it is available wherever access to the distributed ledger database 10 is available. This data is therefore encrypted using either or both a rules database 20.1 and/or mode database 20.2 with further data manipulation such that the precise location and location vectors are entered into the distributed ledger database with known (in accordance to the rules database 20.1 and mode database 20.2 respectively by a rules offset profile 24.1 that is a function of at least one time and location and a mode offset profile 24.2 also as a function of at least one time and location.

Figure 4:
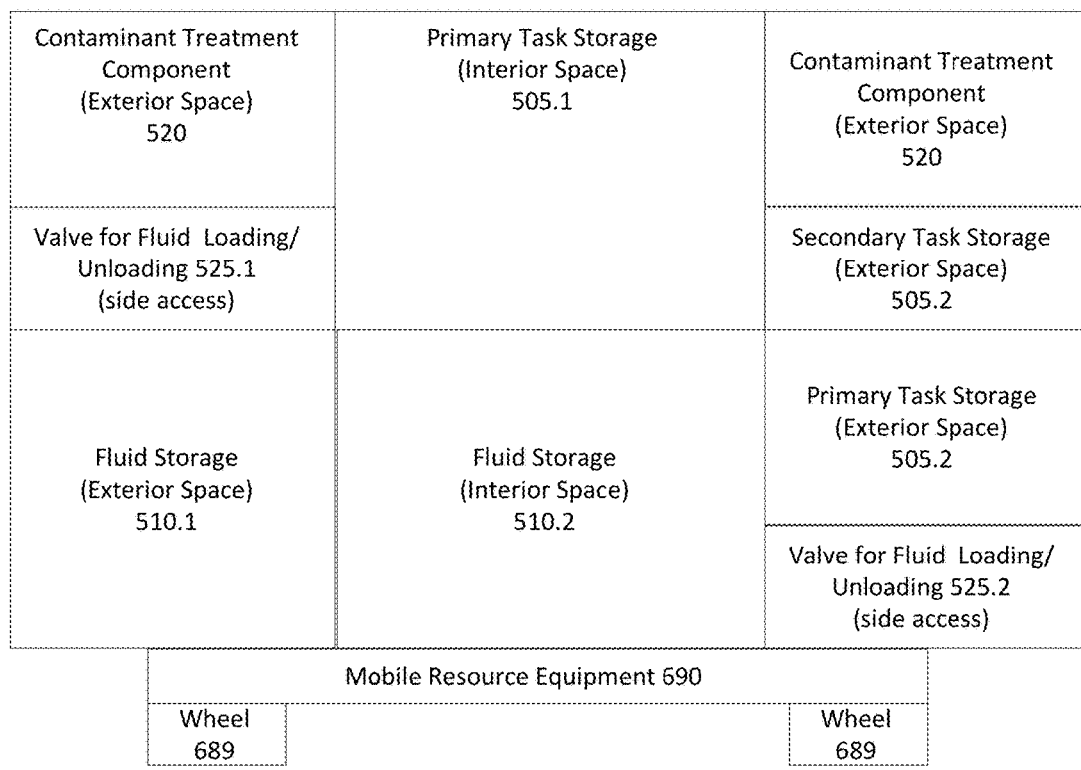
FIG. 4 is a cross-sectional view of a mobile resource.

Turning to FIG. 4, FIG. 4 depicts a cross-section view of the mobile resource equipment 690 (though it is understood that the equipment can be replaced by a person carrying components to execute both a primary task and a secondary task which are shown as components within the primary task storage 505.1 or secondary task storage 505.2 (with further differentiation being between the interior space (i.e., not requiring direct physical access) and exterior space (i.e., requiring direct physical access or having the ability for movement from an interior space to an exterior space through means known in the art). A particularly suitable method of providing access from interior storage to exterior storage (or access) is for fluid storage in an interior space 510.2 through a valve for fluid loading/unloading 525.2. An already exterior fluid storage 510.1 can provide fluid access for fluid loading/unloading via an immediate placed piping and control valve as known in the art 525.1. One exemplary secondary task is decontamination via contaminant treatment component 520 such that movement of the mobile resource equipment 690 can easily achieve its primary tasks with intermittent execution of secondary tasks (e.g., decontamination or cleaning). The mobile resource equipment 690 moves from a first location to a second location via means as known in the art, which includes the most likely wheels 689. It is understood that other means of movement as known in the art include flying, sliding, or conveyors.

Turning to FIG. 5, FIG. 5 depicts the data structure from the mobile resource 690 perspective in its execution of primary tasks 301.1 as shown. It is understood that the data structure is virtually identical for secondary tasks (though not shown). FIG. 5 is exemplary of the use case whereby secondary tasks are cleaning and/or decontaminating of nature (which can be used interchangeably). The mobile resource 690 during its movement between locations as depicted to or from a specific location identified by its location record 302 is through at least one mobility pathway 225 with each occurrence represented by a vector path record 226 within a geofence therefore having a parent-child relationship with that geofence having a geofence record 300. The total area (or volume when decontamination is required on walls as well and not just the floor) requiring decontamination is virtually always greater than the single-pass decontamination achieved by the mobile resource 690. Therefore it is vital and a feature of the invention to maintain a record of each instance of decontaminated area such that subsequent passes within the geofence have a different mobility pathway 225 with the objective of achieving the secondary task (of decontamination) for the entire total area (with minimal additional travel time and distance) so as to not hinder the successful completion of the primary task 301.1 prior to its required completion time of which at least one primary task 301.1 is scheduled/assigned to the specific mobile resource 690. Each mobile resource 690 has an optional operator resource 697 and in virtually all instances has transported resources either that are fundamental to the mobile resource 690 itself or being placed within the various storages as per FIG. 4 in which the primary task is a logistics function including the movement of a fixed asset having a fixed asset record 215 from a first location to a second location or in which the primary task is to perform an operation event having an operating event record 101 on a fixed asset 215 in the location 302. The presence of a guest having a guest record 228 having a mobility pathway 225 takes a specific vector path having a vector path record 226 within a specific geofence having a geofence path record 227 where the guest has a mode identified via a mode record 222 (such that the mode is indicative of the guests specific impact on environmental contamination while protecting the privacy of the guest itself). The guest mobility pathway 225 and its mode 222 records may optionally lead to an unscheduled task 309 that can range from needing immediate attention through an operating event record 101 or remain in-queue on an as required basis. The scheduling of primary tasks is driven, in this use case, by the combination of contaminant events 101 which are further characterized by its contaminant source 105 having distinct though potentially linked via parent-child relationships to at least the primary task 301.1 (so as to define the parameters in which the mobile resource operates it decontamination procedures once assigned to the specific mobile resource) and also linked (though not shown) to the location record 302 in which the contamination took place. The location 302 is within a geofence 300 and both have their records stored within a database 205 that is further located within a database server within a datacenter 200 (that can be on-site or off-site).

Turning to FIG. 6, FIG. 6 has the operational parameters when the mobile resource (though not shown) has its secondary tasks centered around decontamination of assets within a first location to a second location whether it occurs concurrently of primary tasks or if in fact the otherwise secondary tasks become primary tasks through mobile resource reconfiguration from a primary to a secondary task fulfillment device. It is understood that a secondary task can become a primary task with the remaining intent of conducting a decontamination treatment at said location. Parameters include Infectious Disease Source Historic records as function of time "f(t)", Infectious Disease Location Historic f(t), Decontamination Application f(t), Decontamination "Method" Type(s) & Location(s), Mobile Resource Route Historic records f(t), Mobile Resource Decontamination Component(s), Mobile Resource Certification Type(s), Decontamination "Method" Effectiveness per Infectious Disease, Infectious Disease Projected Impact f(t), Projected Decontamination Effectiveness f(t), Infectious Disease Convergence Point(s) f(t), and Probability Mapper per Disease f(t).

Figure 7:
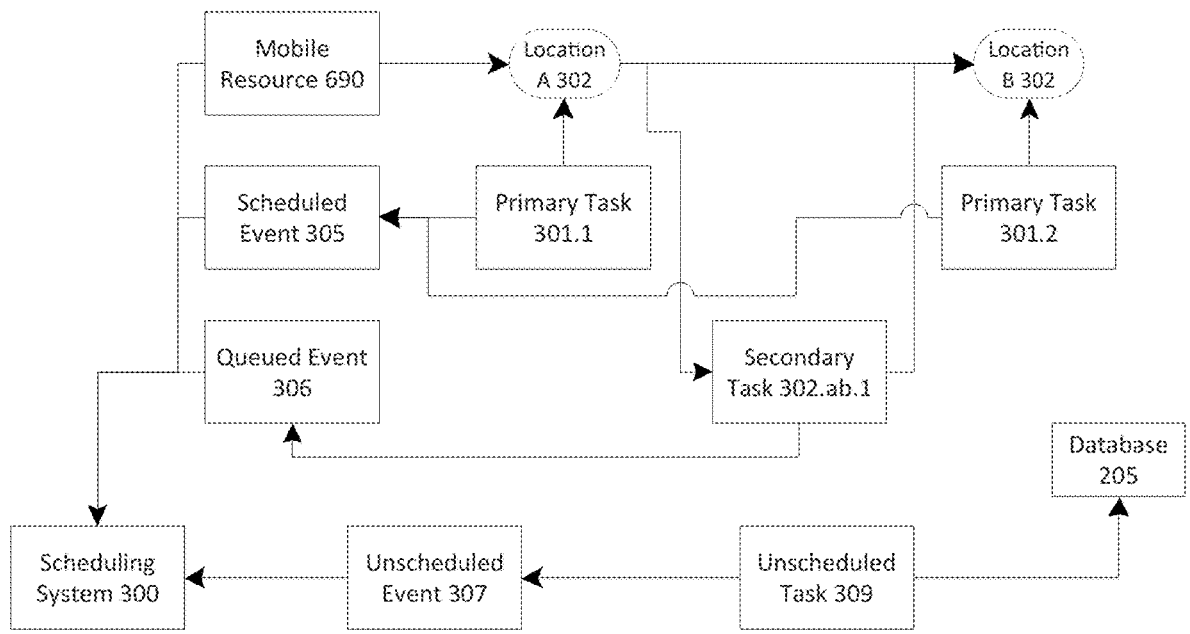
FIG. 7 is a data structure for the mobile resource task scheduling component.

Turning to FIG. 7, FIG. 7 depicts the data structure in a parent-child relationship from a mobile resource 690 perspective notably as it would travel from a first location A302 to second location B302 in its achievement of respectively assigned primary tasks 301.1 and 301.2. The data structure clearly shows at least one secondary task 302.*ab*.1 having a data structure/name indicating that the secondary task is relevant between the first location "A" and the second location "B" which is queued for completion within a queued event 306 series of records. Each of the primary tasks have scheduled execution times within a series of scheduled event 305 records that are further assigned to a specific mobile resource 690 (including the ability to dynamically assign to the mobile resource in real-time based on availability and/or proximity of mobile resource to actual location. The scheduling system 300 coordinates the execution of both primary tasks and secondary tasks all of which have records within the database 205 where each task is first an unscheduled task 309 becoming linked to a specific unscheduled event 307 (as a function of the task itself) and then finally scheduled and assigned to a specific mobile resource 690.

Figure 8:
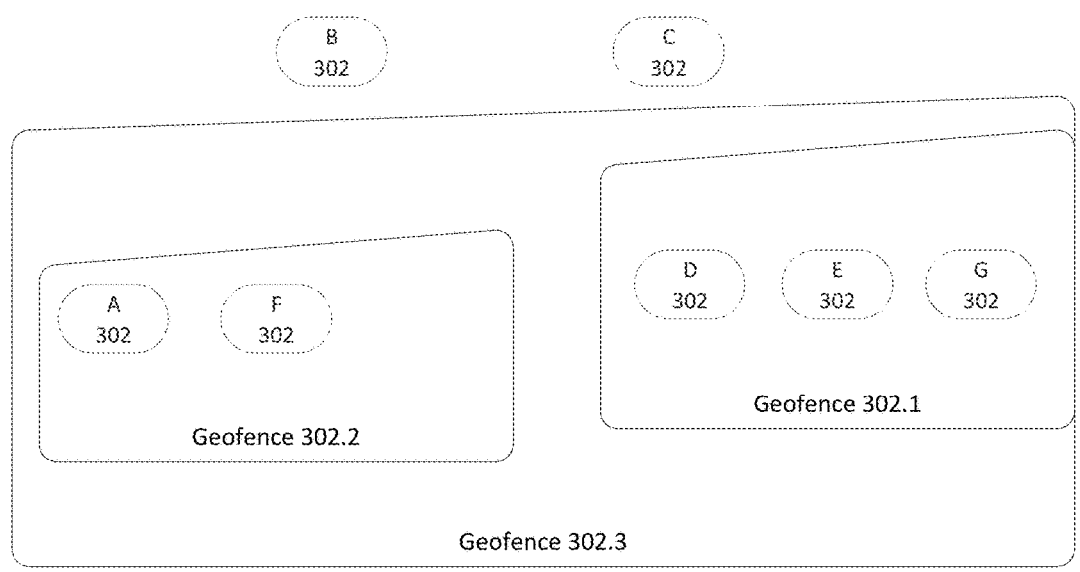
FIG. 8 is a top-view illustration of nested geofences.

Turning to FIG. 8, FIG. 8 depicts the potential (and typical) overlapping of geofences such that exemplary locations B302 and C302 are external of a building represented as a whole by geofence 302.3. The building can have multiple floors or distinct areas, such that the decontamination requirements are distinct, such as a first distinct area being a hospital ICU as location geofence 302.2 having rooms A302 and F302, and a second distinct are being patient rooms in geofence 302.1 having rooms D302, E302, and G302. It is understood that different types of geofences (i.e., physical structures) have the commonality of nested geofences having further nested locations within those geofences.

Figure 9:
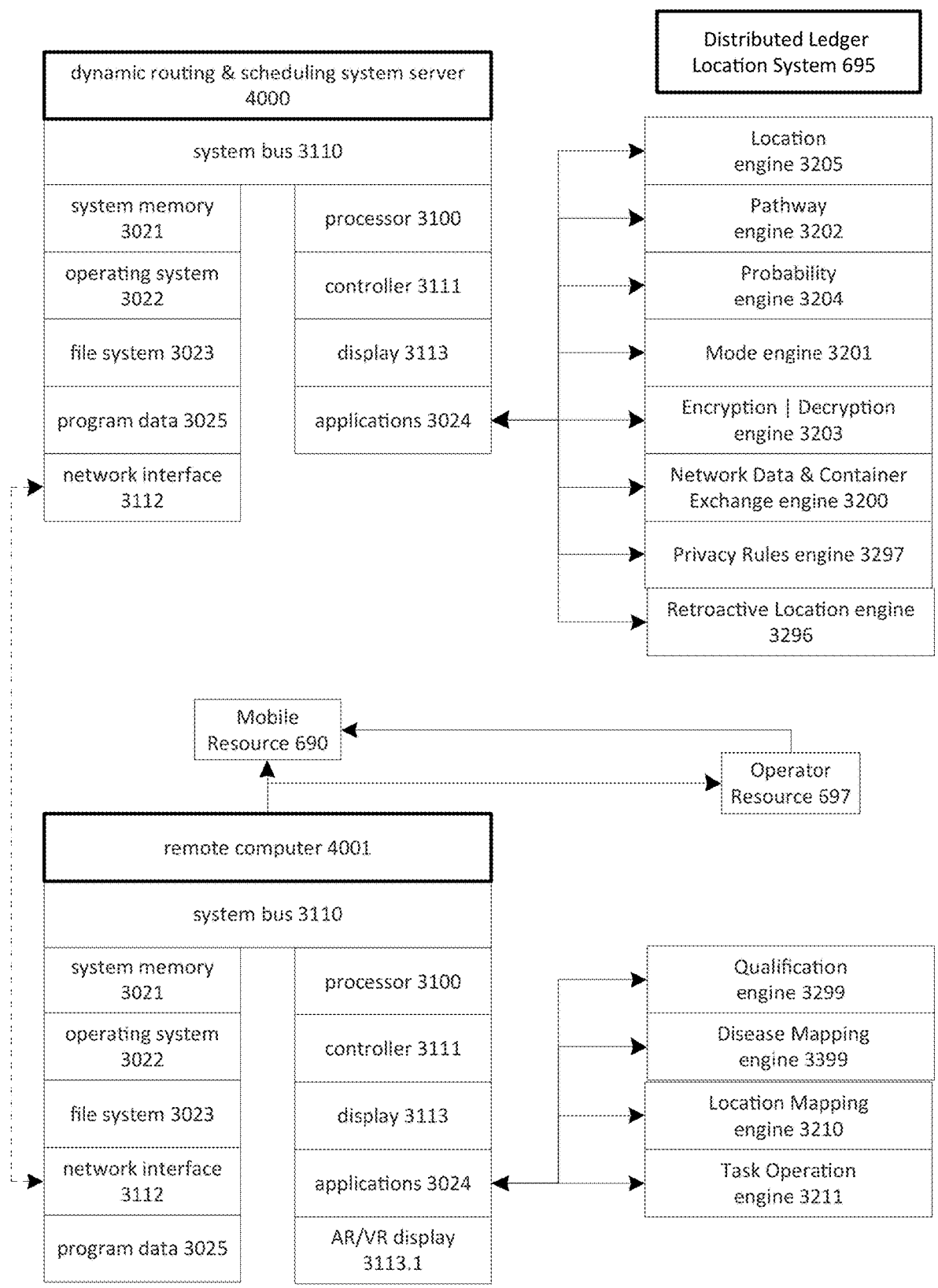
FIG. 9 is a physical and data structure of the mobile system dynamic routing and scheduling system component.

Turning to FIG. 9, FIG. 9 depicts the hardware components for the execution of the mobile resource 690 leveraging the integral dynamic routing and scheduling system server 4000. The mobile resource 690 is at least in intermittent, though preferably continuous, communication with the dynamic routing & scheduling system server 4000 via the wireless network interface 3112. The server 4000 has a system bus 3110 further comprised of system memory 3021, operating system 3022, file system 3023, program data 3025, processor 3100 to execute applications 3024 as coordinated by a controller 3111 with optional display 3113 to an operator coordinating the full execution of the system server (including where the display 3113 is remote from the system server 4000 as known in the art. The system server 4000, though traditional in its nature, the system server 4000 integrates the fundamental and inventive feature of segmenting access to location specific data with authentication as known in the art (e.g., blockchain) though the data itself is encrypted through the encryption (or decrypted through the decryption) engine 3203. The encryption key is further a function of at least one of the mode as established by the mode engine 3201 for each instance of the location as established by the location engine 3205. The privacy rules, as coordinated with the privacy rules engine 3297, establish a second layer of access control by dynamic encryption as a direct function of mode and location. As noted in prior figures, the location utilized is not always precise, therefore the probability engine 3204 is instrumental in improving the accuracy of the location beyond the best available wireless methods (including triangulation) as known in the art through the aforementioned leverage of historic calibration. Additionally, gaps in precise location determination are filled in using the retroactive location engine 3296 to improve not only location precision but also pathways in which the mobile resource 690 travels using the pathway engine 3202. As known in the art data is communicated to networked and distributed hardware, including placing the data in containers as known in the art, through the network data and container exchange engine 3200. The mobile resource 690 can have a co-located or remote operator, such that the mobile resource execution of primary and secondary tasks can be modified via the operator resource 697 using the onboard remote computer 4001. The remote computer 4001 has identical major components in functionality, though understood that the specifications and performance may be different, plus an augmented reality or virtual reality display 3113.1 providing real-time feedback to persons within its current operating vicinity. Each mobile resource 690 has a range of tasks in which it is certified and qualified as coordinated by the qualification engine 3299. Each mobile resource also has a 360-degree noise impact map as both a function of specific operations to fulfill primary and/or secondary tasks and range from mobile resource 690 to other people (e.g., guests, patients, staff, etc.) present as the mobile resource passes by in its movement from a first location to a second location. The disease mapping engine 3399 modulates at least one of the pathways in which the mobile resource takes and/or the execution of secondary tasks along the taken pathway, and/or the speed within the pathway, and/or the speed/rate of task execution so as to minimize the noise impact. The location mapping engine 3210 coordinates the precise pathway executed by the mobile resource 690 such that execution of both primary tasks and secondary tasks are effectively achieved, that being such that secondary tasks are sequenced in accordance to the task operation engine 3211 with further operating parameters as established by the noise impact mapping engine after the qualification engine 3299 validates the ability of the mobile resource to adequately perform its assigned tasks.

Figure 10:
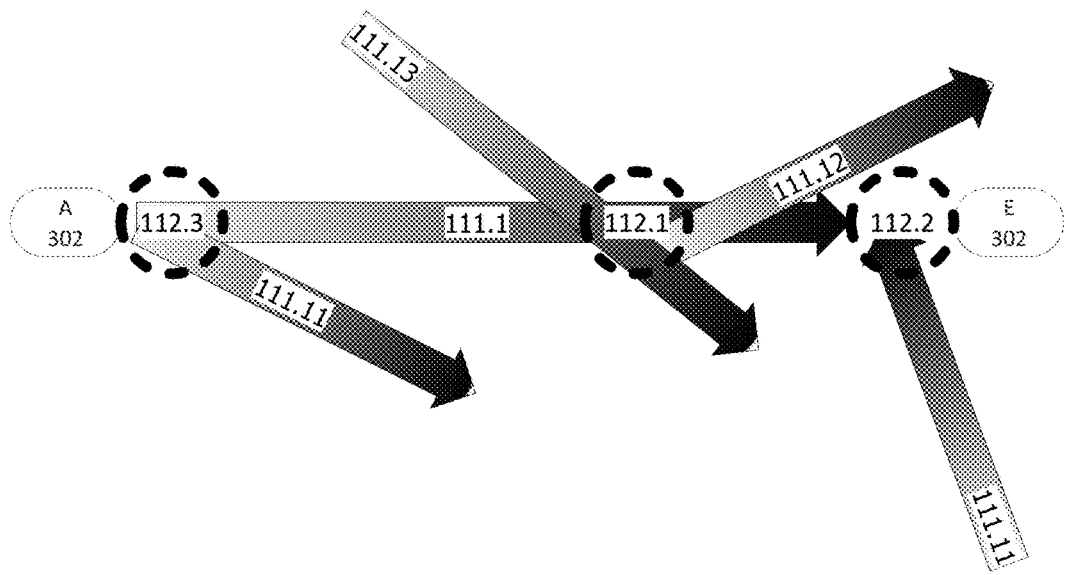
FIG. 10 is a top view illustration depicting vectors converging in both time and space domains.

Turning to FIG. 10, FIG. 10 depicts vectors representing the movement between locations, such as the first location A302 to the second location E302, with each individual vector represented both by directionality and color gradient (in this case as shown in black and white with shades of grey). The exemplary instance shown clearly shows convergence of space and time (as indicated by dashed circles) at convergence point 112.3 for vectors 113.11 and 111.1, as well as convergence point 112.1 between vectors 111.13 and 111.1 (and clearly not 111.12 due to different color, meaning no convergence of time but only space). Convergence point 112.2 at location E302 is for vectors 111.1 and 114.11.

Figure 11:
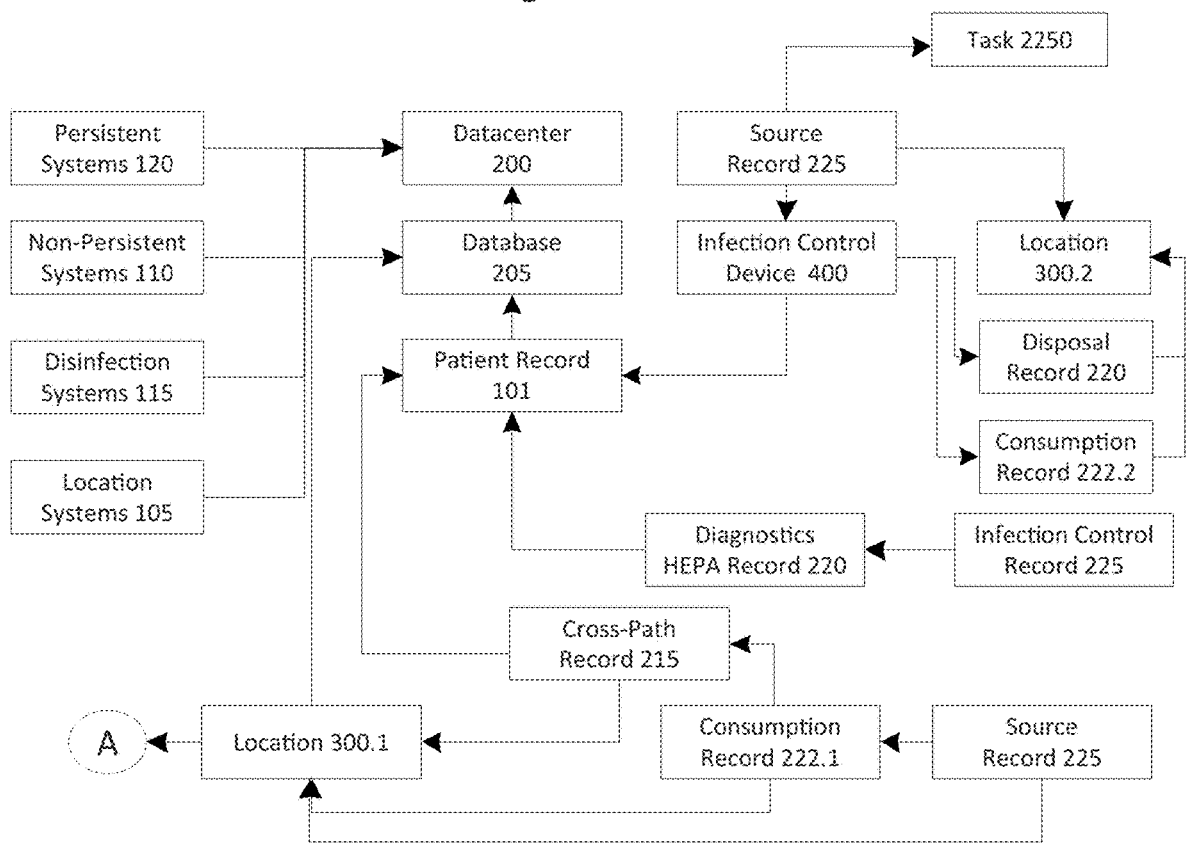
FIG. 11 is a data structure for the mobile resource use case of infectious disease.

Turning to FIG. 11, FIG. 11 depicts the data structure specific to the use case of cleaning/decontamination tasks achieved as predominantly secondary tasks 2250. The establishment of secondary (or primary) tasks are a function of persistent disinfection systems 120, non-persistent systems 110, or general disinfection systems 115 (all having parameters of effectiveness that are disease specific across time since exposure of contaminant and since application of disinfection (whether general, persistent, or non-persistent)) at each location 300.1 coordinated by the location system 105. The aforementioned systems are an integral component of the server system at the datacenter 200 with each record being part of a database 205. Each patient (used interchangeably with any person or source of contamination) record 101 has a record also part of a database 205. Each source of contamination has vector representation across time and space domains with each having a record identifying the cross-contamination pathway 215 further having a parent-child relationship with a specific location 300.1 (that can be further defined as a geofence). Each contamination source (i.e., patient) 101 is characterized by the type of contamination as contained within a diagnostics HEPA record 220 further containing individual records for each disease state in the infection control record 225. The patient disease state can be treated via infection control device 400 such that the present infection control treatment and original source identification of disease state 225 determines the specific nature of tasks 2250 required for reducing cross-contamination. A further feature of the system includes the disposal 220 of materials utilized in the infection control device 400 at a second location 300.2 (or any other location including the same first location) then becoming a potential contamination source at that second location. The treatment of infection control 400 can occur over multiple individual treatments each of which creates a consumption record 222.2. Non-patient specific items can be consumed at a given location 300.1 as indicated by a consumption record 222.1 with an original source record 225. Another exemplary of said location specific consumption can be food (which is subsequently identified as contaminated) with as yet unknown consumer.

Figure 12:
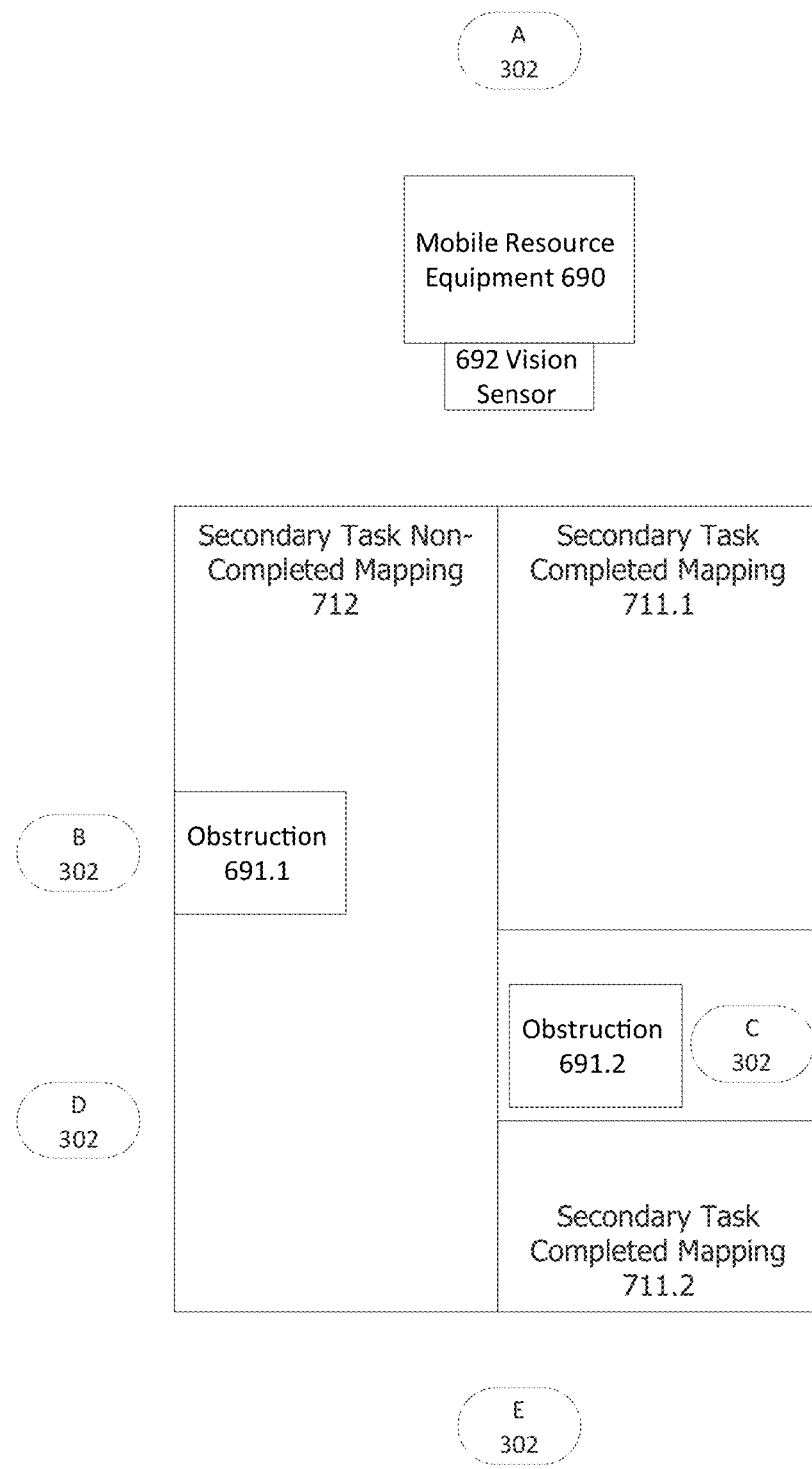
FIG. 12 is a top view of the mobile resource pathway options between a first location and a second location.

Turning to FIG. 12, FIG. 12 depicts the mapping area between a first location A302 having a required first primary task and the ending location E302 having a second primary task with the intermediate locations of B302, C302, and D302 all having consideration of secondary tasks to be completed. In between the first location A302 and the ending location E302 is a mapping of areas in which secondary task has already been completed being the Secondary Task Completed Mapping 711.1 and 711.2, as well as areas in which secondary task has not yet been completed being Secondary Task Non-Completed Mapping 712. The mobile resource 690 is equipped with at least one vision sensor 692 to at the very least determine where obstructions 691.1 and 691.2 exists that trigger dynamic scheduling of secondary tasks by the mobile resource 690 including in instances where delaying travel movement between the first location A302 and ending location E302 after the obstruction 691.1 and/or 691.2 would at worst force the completion of the primary task at ending location E302 to be after its required completion time. Therefore, the routing and scheduling of the secondary tasks are modified in real-time so as to avoid obstructions at least when such delay in travel movement would create missing completion of the primary tasks at ending location E302 (or any subsequent locations in which primary tasks are scheduled) prior to its respective required completion time.

Although the invention has been described in detail, regarding certain embodiments detailed herein, other anticipated embodiments can achieve the same results. Variations and modifications of the present invention will be obvious to those skilled in the art and the present invention is intended to cover in the appended claims all such modifications and equivalents.

What is claimed is:

1. A dynamic cross-contamination reduction control system comprised of an operational device having an at least one touch surface whereby the at least one touch surface is interacted by a physical touch by a first person in a first user session and then subsequently by a second person in a second user session; an at least one pathogen inactivation component to decontaminate the at least one touch surface; a microprocessor controller having an at least one sensor to monitor a last touch by the first person, a first touch by the second person, a running time touch interval between a current time and the time of the last touch by the first person, a starting time of the at least one pathogen inactivation component, a running inactivation process time from the current time and the starting time of the at least one pathogen inactivation component on the at least one touch surface, a pathogen probability function whereby the pathogen probability function is a function of at least one of a duration of time since the time of the last touch by the first person; and a visual indicator that signals to the second person as calculated by the microprocessor controller a visual signal indicating a safer location for the second person to touch the first touch by the second person to reduce cross-contamination probability by at least 5%.

2. The dynamic cross-contamination reduction control system according to claim 1 whereby the at least one touch surface is comprised of an at least two touch segments, whereby a microprocessor monitors the running time touch interval for each of the at least two touch segments, whereby the visual indicator signals to the second person a first segment of the at least two touch segments having a higher pathogen probability function on a real-time basis, and whereby a second segment of the at least two touch segments has a lower pathogen probability function on a real-time basis.

3. The dynamic cross-contamination reduction control system according to claim 2, wherein the at least one touch surface is a graphical user interface, whereby the microprocessor monitors the running time touch interval for each of the at least two touch segments, whereby the visual indicator is in a first position for the first user and in a second position for the second person whereby the microprocessor reconfigures the visual indicator from the first position to the second position when the first person touches the touch surface within the first position during the first user session such that the second user during the second user session doesn't touch the first position.

4. The dynamic cross-contamination reduction control system according to claim 2, wherein the at least one touch surface is a graphical user interface, whereby the microprocessor controller monitors the running time touch interval for each of the at least two touch segments, whereby the visual indicator is in a first position for the first user and in a second position for the second person, whereby the microprocessor reconfigures the visual indicator from the first position to the second position when the first person touches the touch surface within the first position during the first user session such that the second user during the second user session will not touch the first position due to the microprocessor controller reconfiguration of the graphical user interface inactivates the first position as an active at least one touch surface during the second session, and whereby the microprocessor actuates an active pathogen inactivation method over the first position after an end of the first user session.

5. The dynamic cross-contamination reduction control system according to claim 2, whereby the microprocessor controller monitors the running time touch interval for each of the at least two touch segments, whereby the at least one pathogen inactivation component to decontaminate the at least one touch surface is comprised of a persistent coating have efficacy to inactivate an at least one pathogen and an active pathogen inactivation component have efficacy to inactivate the at least one pathogen.

6. The dynamic cross-contamination reduction control system according to claim 5, whereby the microprocessor controller has a probability index of time between the first user session and the second user session, whereby the microprocessor actuates the active pathogen inactivation process when the probability index of time between the first user session and the second user session is less than a time of the active pathogen inactivation component to reach a pathogen inactivation effectiveness function and to reach a pathogen reduction threshold level.

7. The dynamic cross-contamination reduction control system according to claim 2 whereby a second visual indicator signals to the second person the second segment, and whereby the second person makes an active decision to avoid the second segment in favor of the first segment.

8. The dynamic cross-contamination reduction control system according to claim 2 whereby the at least one sensor to monitor a last touch by the first person is a motion sensor having an at least two motion sensitive areas to differentiate when the first person is leaving the operational device and the second person is approaching the operational device.

9. The dynamic cross-contamination reduction control system according to claim 2 further comprising an actuator to move the first segment from a first position to a second position and the second segment from the second position to the first position, an active pathogen inactivation component and a shield whereby the shield is in between the first position and the second position to protect the second person from the active pathogen inactivation component.

10. The dynamic cross-contamination reduction control system according to claim 1 whereby the at least one touch surface has a first touch segment and a second touch segment, whereby the first touch segment has an in-plane thermal barrier in thermal communication with the second touch segment, and whereby the thermal barrier reduces heat transfer between the first touch segment and the second touch segment by greater than 50% in comparison to the heat transfer between the first touch segment and the second touch segment when void of the in-plane thermal barrier in between the first touch segment and the second touch segment.

11. The dynamic cross-contamination reduction control system according to claim 1 whereby the at least one pathogen inactivation component to decontaminate the at least one touch surface is a thermal inactivation component, whereby the thermal inactivation component has a through-plane thermal barrier in thermal communication with both an air or water interface of the operational device and a coating substrate below the at least one touch surface, and whereby the through-plane thermal barrier reduces heat transfer between the thermal inactivation component and the coated substrate by greater than 50% in comparison to the heat transfer between the thermal inactivation component and the coated substrate when void of the through-plane thermal barrier in thermal inactivation component and the coating substrate.

12. The dynamic cross-contamination reduction control system according to claim 11 whereby the thermal inactivation component is comprised of a planar conductivity additive in a persistent coating, whereby the planar conductivity additive is within a bulk portion of the persistent coating, and whereby a non-planar conductivity additive is on the persistent coating in an array pattern whereby the array pattern creates a continuous conductivity circuit.

13. The dynamic cross-contamination reduction control system according to claim 12 whereby the non-planar conductivity additive is a laser induced graphene.

14. A dynamic cross-contamination reduction control system comprised of an operational device having an intermediary non-stationary touch surface whereby the intermediary non-stationary touch surface has a physical touch interaction with a first stationary touch surface and then a second stationary touch surface, an at least one pathogen inactivation component to decontaminate the intermediary non-stationary touch surface after the physical touch interaction of the first stationary touch surface and before the physical touch interaction with the second stationary touch surface; a microprocessor controller having an at least one sensor to monitor the physical touch interaction with the first stationary touch surface, another physical touch interaction with the second stationary touch surface, a running time touch interval between a current time and the time of the physical touch interaction on the first stationary touch surface, a starting time of the at least one pathogen inactivation component, a running inactivation process time from the current time and the starting time of the at least one pathogen inactivation component on the first stationary touch surface, a pathogen probability function whereby the pathogen probability function is a function of at least one of a duration of time since the time of the last touch by the first person; and a visual indicator that signals to the second person as calculated by the microprocessor controller a visual signal indicating a safer location for the second person to touch the first touch by the second person to reduce cross-contamination probability by at least 5%.

15. The dynamic cross-contamination reduction control system according to claim 14 whereby the intermediary non-stationary touch surface has an in-plane thermal barrier in thermal communication with the at least one pathogen inactivation component, and whereby the thermal barrier reduces heat transfer between the operational device and the at least one pathogen inactivation component by greater than 50% in comparison to the heat transfer between the operational device and the at least one pathogen inactivation component when void of the in-plane thermal barrier in between the operational device and the at least one pathogen inactivation component.

16. The dynamic cross-contamination reduction control system according to claim 14 whereby the at least one pathogen inactivation component to decontaminate the at least one touch surface is a thermal inactivation component, whereby the thermal inactivation component has a through-plane thermal barrier in thermal communication with both an air or water interface of the operational device and a coating substrate below the intermediary non-stationary touch surface, and whereby the through-plane thermal barrier reduces heat transfer between the operational device and the intermediary non-stationary touch surface by greater than 50% in comparison to the heat transfer between the thermal inactivation component and the operational device when void of the through-plane thermal barrier in thermal inactivation component and the operational device.

17. The dynamic cross-contamination reduction control system according to claim 14 whereby the thermal inactivation component is comprised of a planar conductivity additive in a persistent coating, whereby the planar conductivity additive is within a bulk portion of the intermediary non-stationary touch surface, and whereby a non-planar conductivity additive is on the intermediary non-stationary touch surface in an array pattern whereby the array pattern creates a continuous conductivity circuit.

18. The dynamic cross-contamination reduction control system according to claim 17 whereby the non-planar conductivity additive is a laser induced graphene.

19. A dynamic cross-contamination reduction control system comprised of an operational device having an at least one touch surface on a graphical user interface whereby the at least one touch surface is interacted by physical touch by a first person in a first user session on a first touch segment at a first position and then subsequently by a second person in a second user session on a second touch segment at a second position; an at least one pathogen inactivation component to decontaminate the at least one touch surface; a microprocessor controller having an at least one sensor to monitor a last touch by the first person, a first touch by the second person, a running time touch interval between a current time and the time of the last touch by the first person, a starting time of the at least one pathogen inactivation component, a running inactivation process time from the current time and the starting time of the at least one pathogen inactivation component on the at least one touch surface, a pathogen probability function whereby the pathogen probability function is a function of at least one of a duration of time since the time of the last touch by the first person; and a visual indicator that signals to the second person as calculated by the microprocessor controller a visual signal indicating a safer location for the second person to touch the first touch by the second person to reduce cross-contamination probability by at least 5%; and the microprocessor controller moves the first touch segment to a second touch segment on a real-time basis in between the first user session and the second user session.

20. The dynamic cross-contamination reduction control system according to claim 19 whereby the at least one pathogen inactivation component is comprised of a planar conductivity additive in a persistent coating, whereby the planar conductivity additive is within a bulk portion of an intermediary non-stationary touch surface, and whereby a non-planar conductivity additive is on the intermediary non-stationary touch surface in an array pattern whereby the array pattern creates a continuous conductivity circuit.

\* \* \* \* \*